(12) United States Patent
Ettare (10) Patent No.: US 7,593,769 B1
(45) Date of Patent: Sep. 22, 2009

(54) SURFACE ELECTROMYOGRAPHY INDEX

(75) Inventor: Ryan Dennis Ettare, Morgan Hill, CA (US)

(73) Assignee: IQ Biolabs, Inc., San Diego, CA (US)

( * ) Notice: Subject to any disclaimer, the term of this patent is extended or adjusted under 35 U.S.C. 154(b) by 0 days.

(21) Appl. No.: 11/741,742

(22) Filed: Apr. 28, 2007

Related U.S. Application Data (63) Continuation of application No. 11/675,048, filed on Feb. 14, 2007, now abandoned.

(60) Provisional application No. 60/773,362, filed on Feb. 14, 2006.

(51) Int. Cl.
*A61B 5/05* (2006.01)

(52) U.S. Cl. ...................................... 600/547

(58) Field of Classification Search ................ 600/300, 600/409, 544–546, 587, 591, 595, 554; 128/898, 128/905; 340/825.19; 341/21; 345/157; 463/36; 607/45
See application file for complete search history.

(56) References Cited

U.S. PATENT DOCUMENTS

| | | | | |
|---|---|---|---|---|
| 4,291,705 A | * | 9/1981 | Severinghaus et al. | 600/546 |
| 5,269,302 A | * | 12/1993 | Swartz et al. | 607/45 |
| 5,474,082 A | * | 12/1995 | Junker | 600/545 |
| 5,513,651 A | | 5/1996 | Cusimano et al. | |
| 5,755,675 A | | 5/1998 | Sihvonen | |
| 5,776,073 A | * | 7/1998 | Garfield et al. | 600/546 |
| 5,964,719 A | * | 10/1999 | Costello et al. | 600/595 |
| 6,453,194 B1 | | 9/2002 | Hill | |
| 6,647,288 B2 | * | 11/2003 | Madill et al. | 600/546 |
| 6,678,549 B2 | | 1/2004 | Cusimano et al. | |
| 7,234,469 B2 | * | 6/2007 | Hanin | 128/898 |

* cited by examiner

*Primary Examiner*—Max Hindenburg
*Assistant Examiner*—Brian Szmal
(74) *Attorney, Agent, or Firm*—Workman Nydegger (57) ABSTRACT

Methods and apparatus for surface electromyography (sEMG) index calculation and applications. The sEMG data points are quantified by accessing sEMG data points describing activity of a muscle. A single value is calculating from the sEMG data points. The single value is calculated using the sEMG data points as an input to a mathematical algorithm. The mathematical algorithm can include an integral. The mathematical algorithm can also include consideration of high points, low points, averages within the sEMG data points, first-order derivatives, second-order derivatives, and other direct or indirect data based at least in part upon sEMG data. The E-index calculated can be used in many applications and in combination with EKG and EEG.

52 Claims, 5 Drawing Sheets

SURFACE ELECTROMYOGRAPHY INDEX

CROSS-REFERENCE TO RELATED APPLICATIONS

This application is a continuation of U.S. patent application Ser. No. 11/675,048 filed on Feb. 14, 2007 now abandoned which claims the benefit of U.S. Provisional Patent Application Ser. No. 60/773,362 filed on Feb. 14, 2006. The contents of both applications are hereby incorporated by reference herein.

BACKGROUND OF THE INVENTION

Surface electromyography (sEMG) data measures muscle activity, typically expressed in microvolts. Two conductive sensors are placed on the skin some distance apart from one another. The potential difference between these two points is measured. Then, some combination of hardware and software amplifies, filters, smoothes, and/or displays the data. Other manipulations of the raw potential difference can be effected either for functional or aesthetic reasons. Display of the data points can involve a stand-alone unit involving an array of LEDs, sound indicators, and/or a computer program that displays a live graph of muscle activity. The most accurate data tends to be of this latter type (i.e., a live graph displayed on computer). However, there has yet to be significant automated algorithmic index-generation from sEMG data.

The subject matter claimed herein is not limited to embodiments that solve any particular disadvantages or that operate only in particular environments such as those described herein. Rather, such environments and disadvantages are provided only to illustrate examples of technology areas in which several embodiments may be practiced.

BRIEF SUMMARY OF THE INVENTION

A method for quantifying sEMG data is disclosed. The method includes accessing sEMG data points describing activity of a muscle. The method further includes calculating a single value from the sEMG data points. The single value is calculated using the sEMG data points as an input to a mathematical algorithm.

Another method for quantifying sEMG data is described. The method includes accessing sEMG data points describing muscular activity of an individual. The method further includes calculating at least one E-index value (also referred to herein as sEMG index and Ettare Index) summarizing the sEMG data points. The E-index value can be calculated based at least in part on an area under a curve representing the sEMG data points, the curve approximating at least a portion of the sEMG data points. The E-index value can also be calculated based at least in part on an area over the curve. The E-index value can be calculated based at least in part on a combination of high points, low points, and averages of multiple data points. The E-index value can also be calculated based at least in part on derivatives, for example first- and second-order derivatives, of a curve representing the sEMG data points, the curve approximating at least a portion of the sEMG data points. Other forms of direct or indirect data based on the sEMG data can also be calculated. The E-index value can be output to an electronic device.

These and other features of the present invention will become more fully apparent from the following description and appended claims, or may be learned by the practice of the invention as set forth hereinafter.

BRIEF DESCRIPTION OF THE DRAWINGS

To further clarify the features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF SEVERAL EMBODIMENTS

The principles of the embodiments described herein describe the structure and operation of several examples used to illustrate the present invention. It should be understood that the drawings are diagrammatic and schematic representations of such example embodiments and, accordingly, are not limiting of the scope of the present invention, nor are the drawings necessarily drawn to scale. Well-known devices and processes have been excluded so as not to obscure the discussion in details that would be known to one of ordinary skill in the art.

Figure 1:
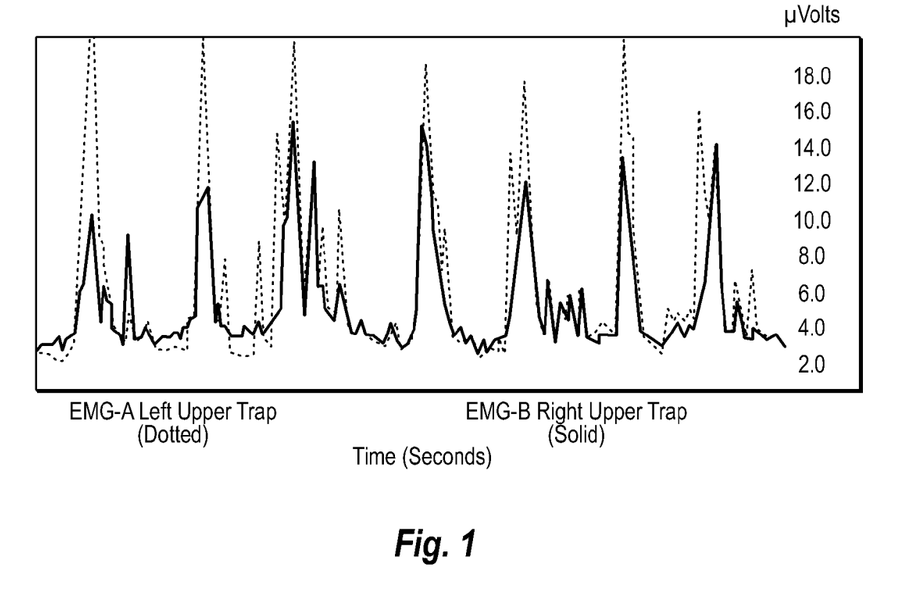
FIG. 1 illustrates an example display of sEMG values over time.

Typically, a healthy muscle in a resting state will show sEMG values around 2 microvolts. During use, the muscle's activity level will spike upward, with values that depend greatly on the muscle in question, the neuromuscular/musculoskeletal health of the individual, and the kind of activity. For example, right and left upper trapezius activity while alternating sitting or standing (body position presumed to be the only variable) may look something like that shown in FIG. 1. The example shown in FIG. 1 illustrates that sEMG values can range from around 5 microvolts to around 14 microvolts in such an example. During intense use, values may shoot up significantly higher, however, possibly even an order of magnitude higher (100 microvolt range).

Figure 2:
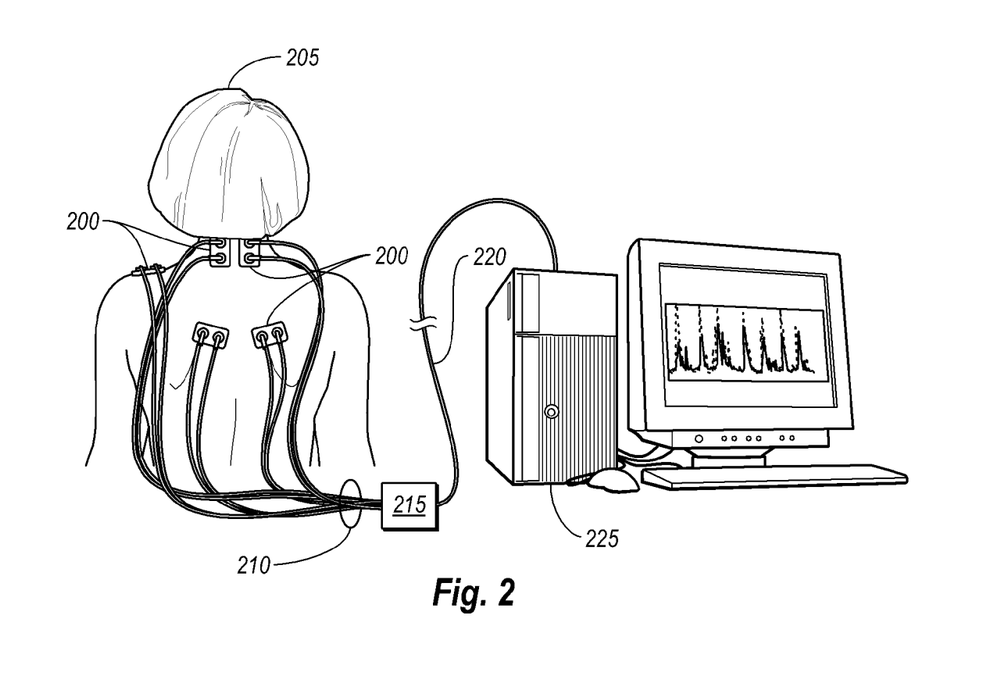
FIG. 2 illustrates a system for collecting sEMG data.

Embodiments disclosed herein include numerical, quantitative assessment of sEMG data using values referred to herein as the sEMG index, Ettare Index, or E-index. The Ettare Index is a term used to relate to index values that more concisely describe muscle activity over time. Put another way, an E-index describes muscle loading, implicit in which is the assumption of a timeframe. The E-index summarizes sEMG information that is comprised of a series of data points. These data points are typically represented in the format (X,Y) (e.g. See FIG. 1). The X axis refers to the point in time in which the value was taken and the Y axis refers to the potential difference of the muscle at that point in time. For example, raw data can be processed according to many different algorithms, yielding a single value. This value, such as a raw number, can then be scaled. For example, the value can be scaled onto a 1-10 range, a 1-100 range, a color scale, a sound scale, or other methods with which to communicate, further process, and/or store the information.

sEMG data is bulky in the sense that thousands of data points comprise a single graph. It is frequently up to the subjective opinion of the observer to assess the state of the muscle based upon the graph. However, according to the teachings herein algorithms can be used to introduce objectivity into sEMG graph interpretation. There are different methods of arriving at this E-index value, which may represent different theories as to the significance of different aspects of an sEMG graph. It is important to note that this invention covers any and all methods of arriving at a single value based upon sEMG data.

sEMG data can be collected using many different systems and apparatuses. For example, referring to FIG. 2, a system for collecting sEMG data is illustrated. The system includes sEMG conductive sensors 200 coupled to various muscles of an individual 205 under test. The sEMG conductive sensors 200 are coupled via wires 210 or wirelessly to a data collection device 215 that is in turn coupled via a wired or wireless connection 220 to a processing device, such as a conventional or special purpose computer 225. The computer 225 includes software and hardware for collecting the sEMG data which may be displayed by the computer 225. The computer 225 further includes software and hardware configured to analyze the sEMG data to calculate E-index value(s) and perform analysis according to the methods disclosed herein. The system illustrated in FIG. 2 can be combined with other apparatus, such as lie detection, motion detection, electrocardiography (EKG), electroencephalography (EEG) devices, and other systems as described in further detail hereinafter.

1. Examples of Methods of E-Index Calculation

Many different methods and algorithms can be used to quantify sEMG graphs into one or more E-Index values. For example, the index calculation can include consideration of an area under a curve. Under this method, an integral of at least a portion of an sEMG graph can be taken or approximated. This approximation can either be standardized with respect to a consistent length of time, for example two minutes of activity, or described in terms of a unit time.

A weighted integral/double integral can also be considered. For example, the area under the weighted integral/double integral curve can be measured under the assumption that the data is most significant when closest to the bottom of the graph. To calculate this, a density gradient is used such that 0 microvolts represents 100% density, and 100 microvolts (arbitrary value for example only) represents 0% density. The density gradient may increase linearly or non linearly (or a combination thereof). The area under the curve is calculated taking this significance density into account. This effectively minimizes the importance of spikes in the graph and emphasizes the troughs.

According to another embodiment, an area over a curve can be used to quantify sEMG graphs. The area over the curve is calculated or estimated by establishing a horizontal line parallel to the x-axis, the height of which is arbitrary—for example determined by the maximum height of the graph, or some distance from it. This area over the curve can be used to numerically represent the results of an sEMG graph. This method also emphasizes the troughs and deemphasizes the spikes in an sEMG graph that may be present.

According to another embodiment, any combination of high data points, low data points, and/or average data points can be used to quantify sEMG graphs. Also, other forms of indirect data may be used, such as derivatives (first, second, etc) of curves approximating at least a portion of an sEMG graph. This embodiment represents a number of different methods that may be varied in terms of the weights, or relative importance, associated with them. High points, low points, and averages of data points are significant values that can be used to calculate E-index variants. A high point (H), or point of inflection in which the first-order derivative changes from positive to negative, represents the height of a spike. A low point (L), or point of inflection in which the derivative changes from negative to positive, represents the depth of a trough. An average (A) is a mean for a given time interval. It is important to note that during calculation of high points and low points, a time interval or sensitivity range should be specified. The broader the range, the greater amount of data is summarized by the E-index. The smaller the time-interval becomes, more the E-index begins to approach an instantaneous rate of muscle loading. There are advantages and disadvantages to each range implementation.

In this method, for each time interval, the high points, low points, and average are calculated. If there are multiple high points and/or multiple low points, the average (or other distribution) of the high points and low points can be calculated and used in the following equation.

$$DH+CL+BA=E$$

where E is the E-index, or sEMG index

The constants, D, C, and B, in the above equation represent the weight, or significance, of the high points, low points, and average, respectively. An example version of this equation is:

$$0.3H+0.6L+0.1A=E$$

This example places 60% significance on the low points, 30% significance on the high points, and 10% significance on the average. Any number of weights can be placed on the different constants D, C, and B in the above equation and any combination of high data points, low data points, average data points, and other direct or indirect data derived from sEMG data can be used, or excluded, from the calculation. In one embodiment D is about equal to about 0.3 C is about equal to about 0.6 and B is about equal to about 0.1.

Other algorithms for calculating E-index values can also include other quantifiable derivations of an area under a curve, an area over a curve, high data points, low data points, and an average of data points. For examples, a ratio of high data points, low data points, and averages of data points can be used to calculate E-index values. Other forms of direct or indirect data based on the sEMG data can also be calculated. Thus, many different algorithms may be implemented to derive E-index values for sEMG data.

2. Processing Multiple Index Values.

The E-index can be calculated for multiple segments. For example, if an individual is being tested over a two-minute time frame, in which there are four 30 second subdivisions which represent four different tasks, the E-index for each task can be calculated. The overall E-index for the complete test can be a simple average, or, if the significance of one task is greater than another, they could be weighted unevenly.

Weighting of the different parameters can be used for multiple muscle groups. For example, if sixteen muscles are being monitored, the E-index can be calculated for each group for a given period of time. These data points for the different muscle groups can then all be averaged together, or, if one muscle group has more significance than another, a weighted average can be calculated. This is useful when trying to determine the likelihood of different events. For example, testing for work-related upper-extremity disorders, specifically some forms of keyboard-induced repetitive strain injuries (RSI), may emphasize testing for overuse of muscles in the wrists and forearms and deemphasize muscles in the lower back.

3. Examples of the Significance and Uses of the E-Index

The E-index can be used to predict an individual's likelihood of developing RSI and related neuromuscular or musculoskeletal injuries that may result in chronic pain, as well as other unrelated conditions and/or symptoms. As shown in several studies, chronic overuse of muscles inflames tissue around muscle spindles creating trigger points. The tissue inflammation affects muscle spindles, inducing pain via interaction with innervated receptors within the spindle. This is thought to be a physiological basis for chronic pain. Therefore, a method of quantifying muscle activity can identify muscles operating above safe levels.

Figure 3:
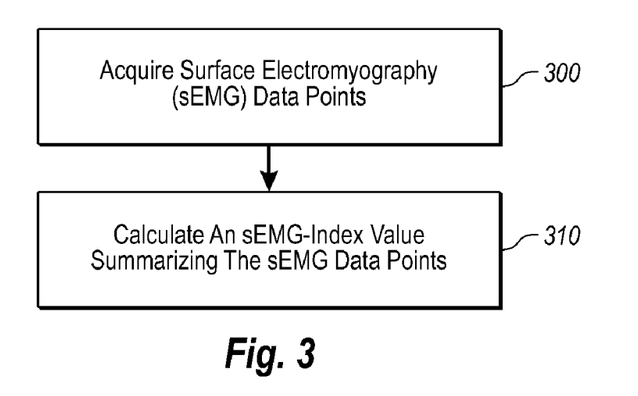
FIG. 3 illustrates a method for predicting an individual's likelihood of developing a medical condition, such as repetitive strain and related injuries.

For example, referring to FIG. 3, a method for predicting an individual's likelihood of developing a medical condition, for example one resulting in chronic pain, is illustrated. sEMG data points are acquired describing muscular activity of the individual (300). The data points can be acquired by placing at least two conductive sensors on the individual's skin some distance apart from one another at a particular location (or multiple locations). The potential difference (voltage) between each pair of points is measured as a single data point and multiple data points are measured over a period of time. The data points can be measured during rest (e.g., while the individual is sitting or lying down) and/or while the individual is performing various tasks. The data points can be stored in computer readable memory and accessed from the computer readable memory for processing and/or display.

An E-index is calculated from the sEMG data points acquired, where the E-index summarizes the sEMG data points acquired (310). The E-index can be calculated based on an area under a curve, wherein the curve approximates at least a portion of the sEMG data points. The E-index can also be calculated based on an area over the curve approximating the sEMG data points. The E-index can also be calculated based on any combination of data including high data point(s), low data point(s), average data point(s), derivatives of various orders, and other forms of direct or indirect data based on sEMG data.

The different data points can be weighted. For example, high data points, low data points, average data points, data points taken during a particular time period, data points taken from a particular muscle group, data points taken while the individual is performing a particular task, and/or data points taken based upon some other criteria can be assigned a weight and the E-index can be calculated taking into consideration these different weights.

Additionally, the E-index serves as a snapshot of muscular health at a given point in time. Snapshots can be used to evaluate individuals and populations of individuals as a one-time evaluation of health, or pre- and post-treatment as discussed in further detail below. Snapshots may also serve to provide a statistical and meaningful basis for describing the efficacy of various treatment methods for RSI and other disorders, such as those involving chronic pain, muscles, biological electrical activity or others.

Figure 4:
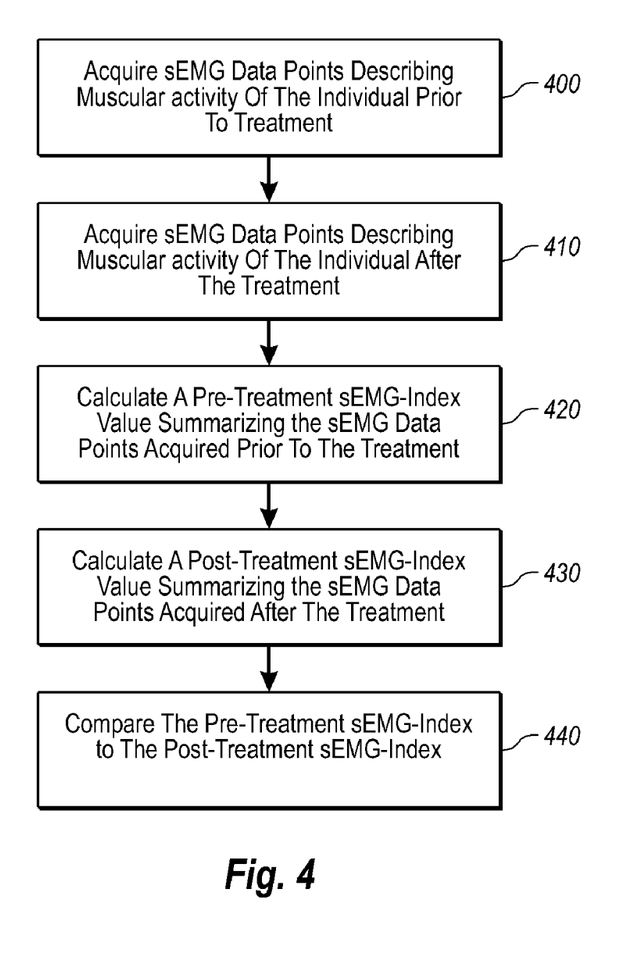
FIG. 4 illustrates a method for evaluating a change in muscle health due to treatment.

For example, a method for evaluating a change in muscular health of an individual before and after treatment is illustrated in FIG. 4. The method can include acquiring sEMG data points describing muscular activity of the individual prior to the treatment (400) and acquiring sEMG data points describing muscular activity of the individual after the treatment (410). A pre-treatment E-index is calculated from the sEMG data points describing muscular activity of the individual prior to the treatment (420). A post-treatment E-index is calculated from the sEMG data points describing muscular activity of the individual after the treatment (430). The pre-treatment E-index is compared to the post-treatment E-index (440) to evaluate the treatment. For example, the comparison can be used to evaluate whether the treatment resulted in an improvement in muscular health by decreasing muscle use during some standardized activity. The E-indexes can be calculated according to any of the algorithms and processes set forth herein.

Figure 5:
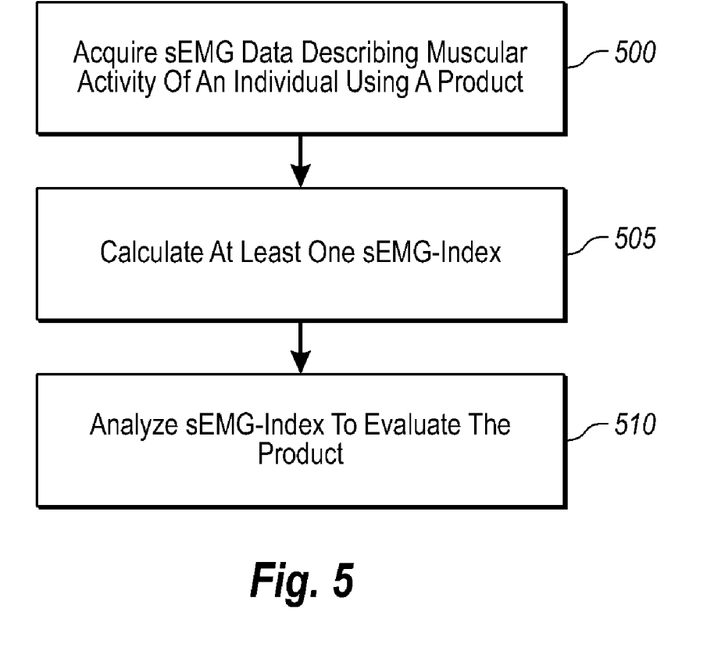
FIG. 5 illustrates a method for evaluating a product.

Similar to evaluating a treatment, the E-index can be use to evaluate a product. The product can be evaluated to determine if the product creates a risk to the health, or determine its ergonomic effectiveness. For example, referring to FIG. 5, a method for evaluating a product is illustrated. The method includes acquiring sEMG data points describing muscular activity of an individual using a product (500). The sEMG data points can be acquired while the individual is using the product (for a fixed period of time, or for a fixed task, for example) to determine the muscular strain on the individual while the individual is using the product. The E-index may be taken for many individuals using the product. The sEMG data points can also be acquired before the individual uses the product and after the individual uses the product to evaluate whether any damage or lasting muscular, neuromuscular, or musculoskeletal change has occurred as a result of the individual's use of the product. Certain muscles may be targeted by the sEMG data points. For example, if the product being evaluated is a computer mouse, certain muscles within the arms of the individual may be targeted or weighted more significantly so as to assess the risk of a repetitive strain injury.

At least one E-index is calculated (505) from the sEMG data points describing muscular activity of the individual during, prior, and/or after use of the product. The at least one E-index is analyzed (510) to evaluate whether the product resulted in a risk to muscular health. The E-index can be calculated according to any of the algorithms set forth herein. The method of FIG. 5 can also be performed for different products and the results compared to evaluate a relative risk between the different products.

The methods disclosed herein can be used to assess the muscular health of a population. For example, the muscular health of a group of individuals, such as the employees of a company or individuals in a locality, may be evaluated using E-index values calculated for each individual do determine an average muscular health of the population. The relative muscular health of the individuals may also be assessed to identify potential individuals at risk, and changes with regard to the at-risk individuals may be implemented to ensure that expenditures related to improving muscular health of the population are spent on individuals with whom the efforts will find the most overall benefit. Thus, a company, insurance company, regulatory body, or other entity interested in maintaining the health of a population can tailor efforts so as to increase the overall effectiveness of such efforts.

Figure 6:
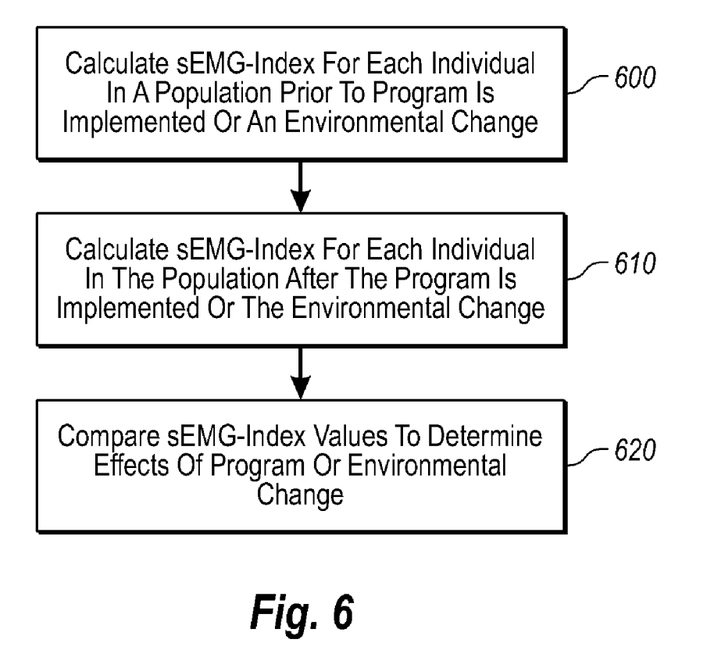
FIG. 6 illustrates a method for determining the effects of a program or environmental change.

The methods disclosed herein may also be used to assess a change in muscular health of a population. A change in muscular health of the population can be assessed, for example, by calculating E-index values for each individual in the population at two points in time (e.g., see FIG. 4). The two points in time may be prior to, and after, a treatment of the population, or a change in an environmental condition for the population. For example, a company may want to implement a program or an environmental change for the company's employees. For example, the company may want to invest in an exercise program or purchase ergonomic equipment for its employees. The company may also want to be able to determine that the program, or environmental change actually improved the muscular health of the company's employees. Therefore, referring to FIG. 6, the company would perform one or more of the methods disclosed herein to calculate E-index values for the employees before the program, or environmental change was implemented (600). The company would also perform one or more of the methods disclosed herein to calculate E-index values for the employees after the program or environmental change was implemented (610). The company would compare the pre-program or pre-environmental change E-index values to post-program or post-environmental change E-index values to determine if the program or environmental change had the desired effects (620). Thus, the company would be able to evaluate whether the program or environmental changes justified their costs in improved muscular health of the population.

Figure 7:
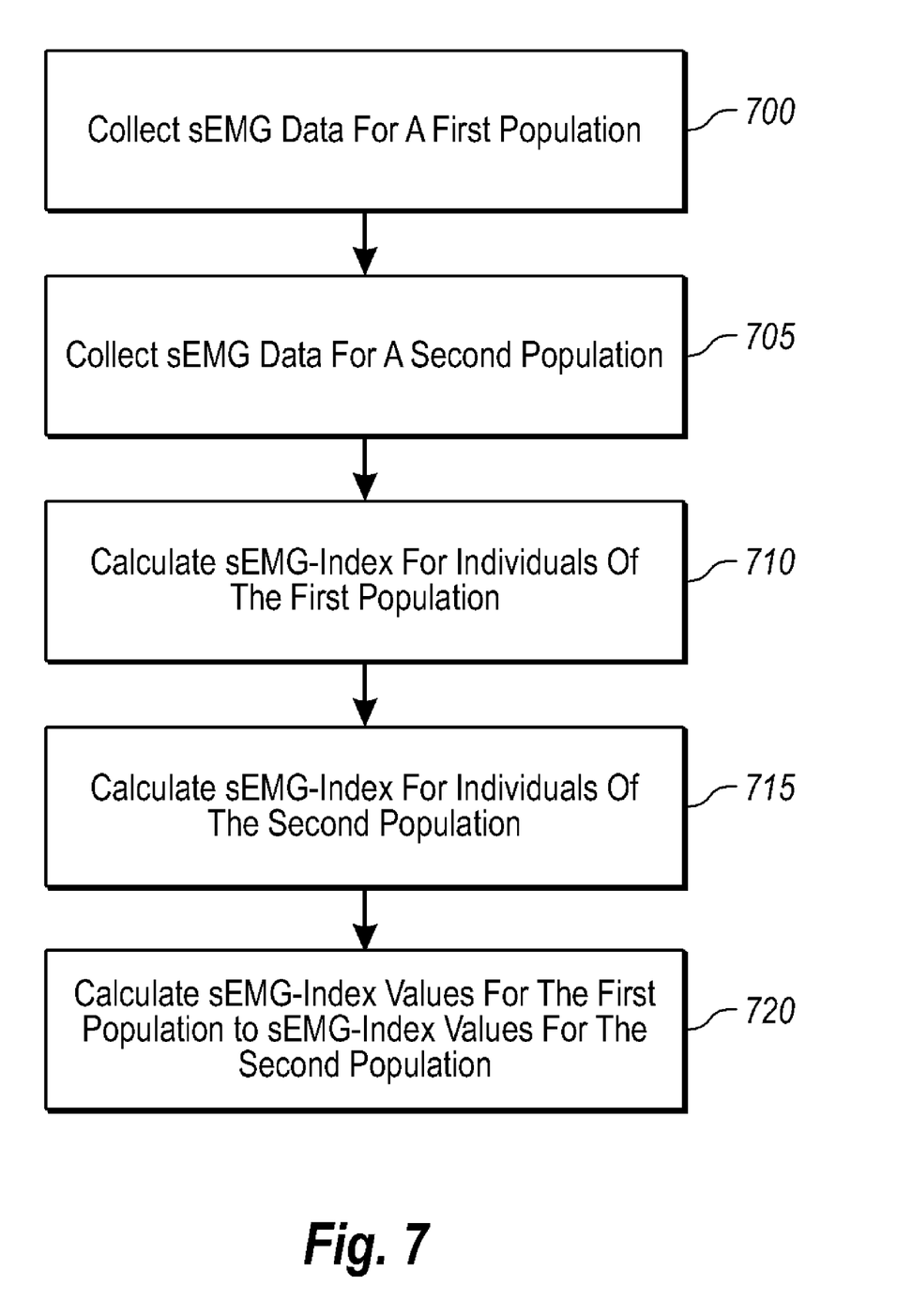
FIG. 7 illustrates a method for assessing the relative muscular health, or change in relative muscular health, between individuals or multiple populations.

Moreover, the methods disclosed herein can be used to assess the relative muscular health, or change in relative muscular health, between multiple populations. For example, referring to FIG. 7, sEMG data is collected for a first population (700). sEMG is also collected for a second population (705). E-index values are calculated for the first population (710) using any of the methods disclosed herein. E-index values are also calculated for the second population (715) according to any of the methods disclosed herein. The E-index values calculated for the first population are compared to the E-index values for the second population (720). The comparison between populations may be assessed to determine relative health risks between the populations. The relative risks may be used for insurance purposes, training effectiveness purposes, or to identify populations having a particular attribute or lifestyle that attributes to muscular unhealthiness or healthiness.

The relative muscular health of populations calculated by E-index values can be used to evaluate the effect of treatments, activity, and environmental conditions. For example, E-index values for each individual within two or more populations can be assessed prior to, and after, a treatment, activity, or change in environmental condition. Thus, the methods of FIGS. 3-7 may be performed at many points in time and the relative change in E-index can be compared over time. The change in E-index values can be compared to determine the effect of the treatment, activity, or change in environmental condition. As such, a more standardized analysis can be conducted over individuals and populations of individuals.

E-index values can be used for many additional applications. For example, E-index values can be used in combination with other technologies to improve lie detection, animation of computer generated characters, to supplement EKG data, and to supplement EEG data.

Lie detection is the practice of determining whether someone is practicing deception. Activities of the body not easily controlled by the conscious mind are compared under different circumstances. Usually this involves asking the subject control questions where the answers are known to the examiner and comparing them to questions where the answers are not known. Lie detection commonly involves a polygraph test, but voice stress analysis may also be implemented. The polygraph detects changes in body functions not easily controlled by the conscious mind such as skin conductivity, heart rate, and respiration. Brain activity, such as changes in brain waves may also be implemented.

According to an embodiment of the present invention, sEMG data may be acquired (e.g., see FIG. 3) and E-index values calculated for determining whether a person is practicing deception. The E-index values can be calculated and analyzed in combination with traditional lie detection practices to determine whether an individual is practicing deception. For example, sEMG sensors may be placed on the individual in areas where muscles may involuntarily indicate that the individual is under stress or to detect a nervous muscular reaction. In one example, the sEMG sensors can be placed about the face of the individual so as to detect changes in involuntary muscular reaction around the individual's eyes, nose, jaw, or involuntary ticks made by the individual while the individual is answering questions. Often, when an individual is lying the individual may involuntarily squint, flick the individual's eyes to different quadrants of the visual field, tense the individual's jaw, flare the individual's nose, or produce other involuntary muscular responses that may be exhibited by changes in E-index values. These E-index values can be analyzed to determine whether the individual is lying when the individual answers particular questions. These E-index values can also be compared with conventional lie detection methods to further substantiate the results of the conventional lie detection methods.

E-index values may also be used for character animation. For example, E-index values can be used in conjunction with motion capture methods. Motion tracking or motion capture started as an analysis tool in biomechanics research, and expanded into education, training, sports, and recently computer animation for cinema and video games as the technology has matured. A performer wears markers near each joint to identify the motion by the positions or angles between the markers. Acoustic, inertial, LED, magnetic or reflective markers, or combinations of any of these, are tracked. The motion capture computer software records the positions, angles, velocities, accelerations and impulses, providing an accurate digital representation of the motion.

In entertainment applications this can reduce the costs of animation which otherwise requires the animator to draw each frame, or with more sophisticated software, key frames which are interpolated by the software. However, motion capture only relates to linear movements of distinct points of the person wearing the markers but does not collect or evaluate information related to muscular changes by the individual.

According to an embodiment, sEMG data is collected describing the muscular activity of an individual. E-index values are calculated from the sEMG data (e.g., see FIG. 3) and the E-index values are used to control an action of an animated character. For example, sEMG sensors may be disposed on an actor's face. The actor may perform a series of actions or simulate a series of emotions. E-index values may be acquired describing the muscular activity of the various facial muscles of the actor. These E-index values can be analyzed to control the facial expressions of an animated character. The facial expression of the animated character can also be combined with previously known methods of motion capture to improve the accuracy of the facial expressions of the animated character.

E-index values can be used to supplement existing methods of EKG and EEG. For example, the calculation of E-index values may be used as a supplement to existing methods for quantitative analysis of EKG data to facilitate checking for heart problems, or to enable different methods of quantitative analysis for the benefit to the field of EKG. Moreover, the calculation of E-index values can be used as a supplement to existing methods for quantitative analysis of EEG data to facilitate checking for abnormal brain activity, or to enable different methods of quantitative analysis for the benefit to the field of EEG.

According to any of the embodiments disclosed herein, an E-index can be output to an electronic device. For example, an E-index can be output to a display, can be stored in memory, can be printed, or output in any other manner.

Embodiments within the scope of embodiments illustrated herein can also include computer-readable media for carrying or having computer-executable instructions or data structures stored thereon for performing the methods disclosed herein. For example, these computer-executable instructions can be configured to cause a computer or other device to gather sEMG data and/or to calculate E-index values. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions such as those disclosed herein.

Figure 8:
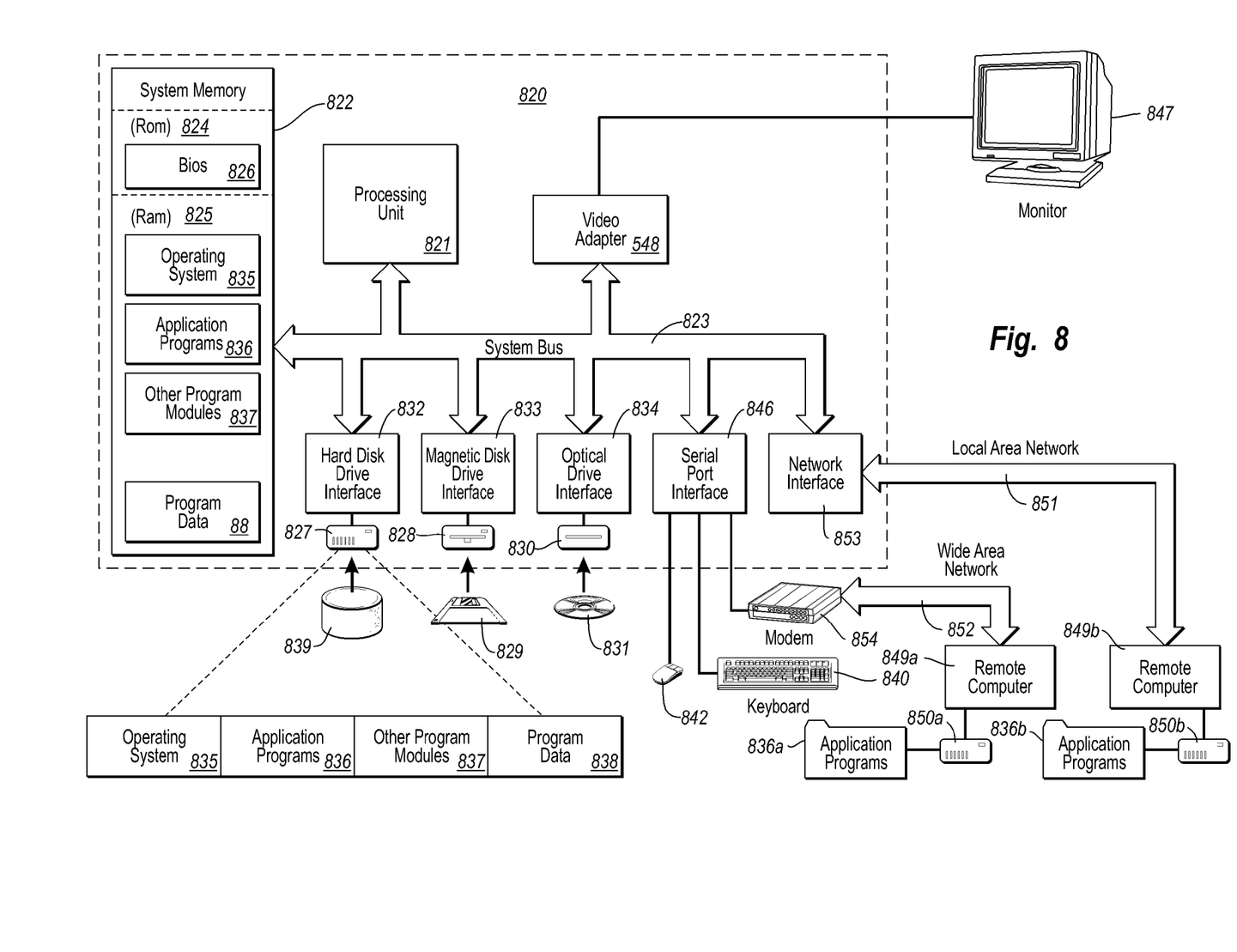
FIG. 8 provides a brief, general description of a suitable computing environment in which several embodiments may be implemented.

FIG. 8 and the following discussion are intended to provide a brief, general description of a suitable computing environment in which several embodiments may be implemented. Although not required, several embodiments will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those skilled in the art will appreciate that the embodiments illustrated herein may be practiced in network computing environments with many types of computer system configurations, including personal computers, hand-held devices, multi-processor systems, microprocessor-based or programmable consumer electronics, network PCs, mini-computers, mainframe computers, and the like. Several embodiments may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 8, an example of a system for implementing several embodiments includes a general purpose computing device in the form of a conventional computer 820, including a processing unit 821, a system memory 822, and a system bus 823 that couples various system components including the system memory 822 to the processing unit 821. The system bus 823 may be any of several types of bus structures including a memory bus or memory controller, a peripheral bus, and a local bus using any of a variety of bus architectures. The system memory includes read only memory (ROM) 824 and random access memory (RAM) 825. A basic input/output system (BIOS) 826, containing the basic routines that help transfer information between elements within the computer 820, such as during start-up, may be stored in ROM 824.

The computer 820 may also include a magnetic hard disk drive 827 for reading from and writing to a magnetic hard disk 839, a magnetic disk drive 828 for reading from or writing to a removable magnetic disk 829, and an optical disk drive 830 for reading from or writing to removable optical disk 831 such as a CD ROM or other optical media. The magnetic hard disk drive 827, magnetic disk drive 828, and optical disk drive 830 are connected to the system bus 823 by a hard disk drive interface 832, a magnetic disk drive-interface 833, and an optical drive interface 834, respectively. The drives and their associated computer-readable media provide nonvolatile storage of computer-executable instructions, data structures, program modules and other data for the computer 820. Although the exemplary environment described herein employs a magnetic hard disk 839, a removable magnetic disk 829 and a removable optical disk 831, other types of computer readable media for storing data can be used, including magnetic cassettes, flash memory cards, digital versatile disks, Bernoulli cartridges, RAMs, ROMs, and the like.

Program code means comprising one or more program modules may be stored on the hard disk 839, magnetic disk 829, optical disk 831, ROM 824 or RAM 825, including an operating system 835, one or more application programs 836, other program modules 837, and program data 838. A user may enter commands and information into the computer 820 through keyboard 840, pointing device 842, or other input devices (not shown), such as a microphone, joy stick, game pad, satellite dish, scanner, or the like. These and other input devices are often connected to the processing unit 821 through a serial port interface 846 coupled to system bus 823. Alternatively, the input devices may be connected by other interfaces, such as a parallel port, a game port or a universal serial bus (USB). A monitor 847 or another display device is also connected to system bus 823 via an interface, such as video adapter 848. In addition to the monitor, personal computers typically include other peripheral output devices (not shown), such as speakers and printers.

The computer 820 may operate in a networked environment using logical connections to one or more remote computers, such as remote computers 849a and 849b. Remote computers 849a and 849b may each be another personal computer, a server, a router, a network PC, a peer device or other common network node, and typically include many or all of the elements described above relative to the computer 820.

When used in a LAN networking environment, the computer 820 is connected to the local network 851 through a network interface or adapter 853. When used in a WAN networking environment, the computer 820 may include a modem 854, a wireless link, or other means for establishing communications over the wide area network 852, such as the Internet. The modem 854, which may be internal or external, is connected to the system bus 823 via the serial port interface 846. In a networked environment, program modules depicted relative to the computer 820, or portions thereof, may be stored in the remote memory storage device. It will be appreciated that the network connections shown are examples and other means of establishing communications over wide area network 852 for calculating the E-indexes and performing the methods disclosed herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Detailed descriptions of apparatus and processing techniques known in the field of the invention to one of ordinary skill in the art have been excluded.

I claim:

1. A method for quantifying surface electromyography (sEMG) data acquired from an individual using one or more sensors, the method comprising:
    a processor accessing sEMG data points describing muscular activity of the individual, the sEMG data points being acquired from the individual using the one or more sensors;
    the processor assigning weights to at least two different muscle groups; and
    the processor calculating at least one E-index value summarizing the sEMG data points comprising:
        calculating the index value based at least in part on an area under a curve, the curve approximating at least a portion of the sEMG data points;
        calculating the index value based at least in part on an area over the curve; or
        calculating the index value based at least in part on a combination of a high data point, a low data point, an average of multiple data points, and/or a derivative of one or more order.

2. A method according to claim 1, wherein calculating the at least one index value comprises:
    calculating the index value based at least in part on an average of multiple high data points or an average of multiple low data points.

3. A method according to claim 1, wherein the area under the curve or the area over the curve is calculated by taking an integral of at least a portion of an sEMG graph representing the sEMG data points.

4. A method according to claim 1, wherein at least two index values are calculated at different time intervals.

5. A method according to claim 4, wherein the time interval for at least two index values corresponds to a different task performed by the individual.

6. A method according to claim 1, wherein an sEMG data point or an E-index value of a muscle group or groups in the individual's forearm and wrist is emphasized to estimate a likelihood of repetitive strain injury.

7. A method for assessing a medical condition comprising:
    performing the method of claim 1; and
    the processor comparing E-index with a result of electrocardiography and/or electroencephalography to assess the medical condition.

8. A method for evaluating health for a population of individuals, comprising performing the method of claim 1 for each individual in the population.

9. A method for comparing the health of multiple populations comprising:
    performing the method of claim 8 for individuals in a first population;
    performing the method of claim 8 for individuals in a second population; and
    the processor comparing the E-indexes for the individuals of the first population to the E-indexes for the individuals of the second population.

10. A method for assessing a likelihood of developing a medical condition, comprising:
    performing the method of claim 1; and
    the processor comparing the calculated E-index value for the individual to E-index values of other individuals to assess the relative likelihood of developing the medical condition.

11. A method according to claim 10, wherein the medical condition is a repetitive strain injury, repetitive motion injury, cumulative trauma disorder, or work-related upper extremity disorder.

12. A method for evaluating a risk associated with a product, comprising:
    performing the method of claim 1 for several individuals before, during, and/or after the individual uses the product to calculate an E-index for each individual; and
    the processor assessing the risk associated with the product based on the E-index calculated for each individual.

13. A method according to claim 12, wherein the risk associated with the product is a health hazard due to an ergonomic factor.

14. A method for detecting a false response, comprising:
    performing the method of claim 1, wherein the E-index calculated relates to an involuntary muscle response of the individual; and
    the processor detecting whether the response was false based at least in part on the E-index calculated.

15. A method for detecting muscle response to control an animated character, the method comprising:
    performing the method of claim 1; and
    the processor associating the E-index with an action of the animated character.

16. A method according to claim 1, further comprising acquiring the sEMG data from the individual.

17. A computer readable medium having computer executable instructions stored on the computer readable medium, the executable instructions being configured to cause a computer to perform the acts of claim 1 when executed by the computer.

18. A method for quantifying surface electromyography (sEMG) data acquired from an individual using one or more sensors, the method comprising:
    a processor accessing sEMG data points describing muscular activity of the individual, the sEMG data points being acquired from the individual using the one or more sensors;
    the processor calculating at least one E-index value summarizing the sEMG data points, comprising:
        calculating the index value based at least in part on an area under a curve, the curve approximating at least a portion of the sEMG data points, or
        calculating the index value based at least in part on an area over the curve, wherein the area under the curve or the area over the curve is calculated by taking a weighted integral or double integral of at least a portion of an sEMG graph representing the sEMG data points.

19. A method according to claim 18, wherein at least two index values are calculated at different time intervals.

20. A method according to claim 19, wherein the time interval for at least two index values corresponds to a different task performed by the individual.

21. A method for assessing a medical condition comprising:
performing the method of claim 18; and
the processor comparing the E-index with a result of electrocardiography and/or electroencephalography to assess the medical condition.

22. A method for evaluating a change in muscular health of the individual due to treatment, the method comprising:
performing the method of claim 18 prior to the treatment to calculate a pre-treatment E-index value;
performing the method of claim 18 after the treatment to calculate a post-treatment E-index value; and
the processor comparing the pre-treatment E-index value to the post-treatment E-index value to evaluate a change in muscular health and/or state due to the treatment.

23. A method according to claim 22, wherein at least one pre-treatment index value and post treatment index value are calculated for at least two different muscle groups.

24. A method for evaluating health for a population of individuals, comprising performing the method of claim 18 for each individual in the population.

25. A method for comparing the health of multiple populations comprising:
performing the method of claim 24 for individuals in a first population;
performing the method of claim 24 for individuals in a second population; and
the processor comparing the E-indexes for the individuals of the first population to the E-indexes for the individuals of the second population.

26. A method for assessing a likelihood of developing a medical condition, comprising:
performing the method of claim 18; and
the processor comparing the calculated E-index value for the individual to E-index values of other individuals to assess the relative likelihood of developing the medical condition.

27. A method according to claim 26, wherein the medical condition is a repetitive strain injury, repetitive motion injury, cumulative trauma disorder, or work-related upper extremity disorder.

28. A method for evaluating a risk associated with a product, comprising:
performing the method of claim 18 for several individuals before, during, and/or after the individual uses the product to calculate an E-index for each individual; and
the processor assessing the risk associated with the product based on the E-index calculated for each individual.

29. A method according to claim 28, wherein the risk associated with the product is a health hazard due to an ergonomic factor.

30. A method for detecting a false response, comprising:
performing the method of claim 18, wherein the E-index calculated relates to an involuntary muscle response of the individual; and
the processor detecting whether the response was false based at least in part on the E-index calculated.

31. A method for detecting muscle response to control an animated character, the method comprising:
performing the method of claim 18; and
the processor associating the E-index with an action of the animated character.

32. A method according to claim 18, further comprising acquiring the sEMG data from the individual.

33. A computer readable medium having computer executable instructions stored on the computer readable medium, the executable instructions being configured to cause a computer to perform the acts of claim 18 when executed by the computer.

34. A method for quantifying surface electromyography (sEMG) data acquired from an individual using one or more sensors, the method comprising:
a processor accessing sEMG data points describing muscular activity of the individual, the sEMG data points being acquired from the individual using the one or more sensors;
the processor calculating at least one E-index value summarizing the sEMG data points, wherein calculating the at least one index value comprises:
calculating the index value based at least in part on a combination of a high data point (H), a low data point (L), and an average data point (A) according to the following equation:

$$DH+CL+BA=E$$

where D, C, and B describe weights assigned to the high data point, low data point, and average data point.

35. A method according to claim 34, wherein D is about equal to about 0.3, C is about equal to about 0.6, and B is about equal to about 0.1.

36. A method according to claim 34, wherein at least two index values are calculated at different time intervals.

37. A method according to claim 36, wherein the time interval for at least two index values corresponds to a different task performed by the individual.

38. A method for assessing a medical condition comprising:
performing the method of claim 34; and
the processor comparing the E-index with a result of electrocardiography and/or electroencephalography to assess the medical condition.

39. A method for evaluating a change in muscular health of the individual due to treatment, the method comprising:
performing the method of claim 34 prior to the treatment to calculate a pre-treatment E-index value;
performing the method of claim 34 after the treatment to calculate a post-treatment E-index value; and
the processor comparing the pre-treatment E-index value to the post-treatment E-index value to evaluate a change in muscular health and/or state due to the treatment.

40. A method according to claim 39, wherein at least one pre-treatment index value and post treatment index value are calculated for at least two different muscle groups.

41. A method for evaluating health for a population of individuals, comprising performing the method of claim 34 for each individual in the population.

42. A method for comparing the health of multiple populations comprising:
performing the method of claim 41 for individuals in a first population;
performing the method of claim 41 for individuals in a second population; and
the processor comparing the E-indexes for the individuals of the first population to the E-indexes for the individuals of the second population.

43. A method for assessing a likelihood of developing a medical condition, comprising:
performing the method of claim 34; and
the processor comparing the calculated E-index value for the individual to E-index values of other individuals to assess the relative likelihood of developing the medical condition.

44. A method according to claim 43, wherein the medical condition is a repetitive strain injury, repetitive motion injury, cumulative trauma disorder, or work-related upper extremity disorder.

45. A method for evaluating a risk associated with a product, comprising:
performing the method of claim 34 for several individuals before, during, and/or after the individual uses the product to calculate an E-index for each individual; and
the processor assessing the risk associated with the product based on the E-index calculated for each individual.

46. A method according to claim 45, wherein the risk associated with the product is a health hazard due to an ergonomic factor.

47. A method for detecting a false response, comprising:
performing the method of claim 34, wherein the E-index calculated relates to an involuntary muscle response of the individual; and
the processor detecting whether the response was false based at least in part on the E-index calculated.

48. A method for detecting muscle response to control an animated character, the method comprising:
performing the method of claim 34; and
the processor associating the E-index with an action of the animated character.

49. A method according to claim 34, further comprising acquiring the sEMG data from the individual.

50. A computer readable medium having computer executable instructions stored on the computer readable medium, the executable instructions being configured to cause a computer to perform the acts of claim 34 when executed by the computer.

51. A method for evaluating a change in muscular health of the individual due to treatment, the method comprising:
performing the method of claim 1 prior to the treatment to calculate a pre-treatment E-index value;
performing the method of claim 1 after the treatment to calculate a post-treatment E-index value; and
the processor comparing the pre-treatment E-index value to the post-treatment E-index value to evaluate a change in muscular health and/or state due to the treatment.

52. A method according to claim 51, wherein at least one pre-treatment index value and post treatment index value are calculated for at least two different muscle groups.

* * * * *